(12) United States Patent
Neumann

(10) Patent No.: US 11,386,477 B2
(45) Date of Patent: Jul. 12, 2022

(54) METHODS AND SYSTEMS FOR GEOGRAPHICALLY TRACKING NOURISHMENT SELECTION

(71) Applicant: KPN Innovations, LLC, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 16/886,673

(22) Filed: May 28, 2020

(65) Prior Publication Data

US 2021/0374826 A1  Dec. 2, 2021

(51) Int. Cl.
| | |
|---|---|
| *G06Q 30/00* | (2012.01) |
| *G06Q 30/06* | (2012.01) |
| *G16H 20/60* | (2018.01) |
| *G16H 50/20* | (2018.01) |
| *G16H 50/30* | (2018.01) |
| *G01C 21/36* | (2006.01) |

(Continued)

(52) U.S. Cl.
CPC ..... *G06Q 30/0631* (2013.01); *G01C 21/3679* (2013.01); *G06N 20/00* (2019.01); *G16H 20/60* (2018.01); *G16H 50/20* (2018.01); *G16H 50/30* (2018.01); *G16H 50/70* (2018.01); *H04L 67/306* (2013.01); *H04W 4/023* (2013.01); *H04W 4/029* (2018.02)

(58) Field of Classification Search
CPC .... G06Q 30/0631; G16H 50/30; G16H 50/70; G16H 50/20; G16H 50/60; H04L 67/306; G01C 21/3679; G06N 20/00; H04W 4/029; H04W 4/023
See application file for complete search history.

(56) References Cited

U.S. PATENT DOCUMENTS

| | | | |
|---|---|---|---|
| 2001/0025279 A1 | 9/2001 | Krulak et al. | |
| 2003/0036848 A1* | 2/2003 | Sheha | G08G 1/0962 340/990 |

(Continued)

OTHER PUBLICATIONS

Hsiao, Jen-Hao, and Henry Chang. "SmartDiet: A personal diet consultant for healthy meal planning." 2010 IEEE 23rd International Symposium on Computer-Based Medical Systems (CBMS). IEEE, 2010. (Year: 2010).*

*Primary Examiner* — Matthew E Zimmerman
(74) *Attorney, Agent, or Firm* — Caldwell Intellectual Property Law; Katherine Rubino

(57) ABSTRACT

A system for geographically tracking nourishment selection including a computing device configured to receive a location from a user device associated with a user; determine a plurality of nourishment possibilities within the location; locate a performance character associated with the user, wherein the performance character contains a nourishment score; generate a user profile wherein the user profile comprises the location, the plurality of nourishment possibilities, and the performance character; generate a selector machine-learning process, wherein the selector machine-learning process utilizes the user profile as an input, and outputs a plurality of corresponding nourishment possibility indexes; and grade the plurality of nourishment possibilities using the plurality of corresponding nourishment possibility indexes.

20 Claims, 7 Drawing Sheets

(51) Int. Cl.
    *G06N 20/00*     (2019.01)
    *H04W 4/029*     (2018.01)
    *H04L 67/306*     (2022.01)
    *H04W 4/02*     (2018.01)
    *G16H 50/70*     (2018.01)

(56) References Cited

U.S. PATENT DOCUMENTS

| | | | |
|---|---|---|---|
| 2003/0208409 A1* | 11/2003 | Mault | G06Q 30/0639 705/26.9 |
| 2011/0318717 A1* | 12/2011 | Adamowicz | G16H 20/60 434/127 |
| 2012/0172027 A1 | 7/2012 | Partheesh | |
| 2012/0239683 A1 | 9/2012 | Starkman | |
| 2012/0303638 A1* | 11/2012 | Bousamra | G16H 20/60 707/751 |
| 2014/0100859 A1 | 4/2014 | Zhu | |
| 2014/0164118 A1 | 6/2014 | Polachi | |
| 2014/0310808 A1* | 10/2014 | Yao | G06F 21/566 726/22 |
| 2015/0243186 A1 | 8/2015 | Eberhardt et al. | |
| 2016/0026491 A1* | 1/2016 | Razin | G06F 9/505 718/1 |
| 2018/0004914 A1* | 1/2018 | Abujbara | G16H 20/60 |
| 2020/0075153 A1 | 3/2020 | Murdoch et al. | |

\* cited by examiner

METHODS AND SYSTEMS FOR GEOGRAPHICALLY TRACKING NOURISHMENT SELECTION

FIELD OF THE INVENTION

The present invention generally relates to the field of nourishment. In particular, the present invention is directed to methods and systems for geographically tracking nourishment selection.

BACKGROUND

Locating and understanding availability and reliability of nourishment possibilities can be challenging. Further, identifying nourishment providers that are situated in a particular location and able to accommodate a user's individual needs can be difficult.

SUMMARY OF THE DISCLOSURE

In an aspect, a system for geographically tracking nourishment selection the system comprising a computing device configured to receive a location from a user device associated with a user; determine a plurality of nourishment possibilities within the location; locate a performance character associated with the user, wherein the performance character contains a nourishment score; generate a user profile wherein the user profile comprises the location, the plurality of nourishment possibilities, and the performance character; generate a selector machine-learning process, wherein the selector machine-learning process utilizes the user profile as an input, and outputs a plurality of corresponding nourishment possibility indexes; and grade the plurality of nourishment possibilities using the plurality of corresponding nourishment possibility indexes.

In an aspect, a method of geographically tracking nourishment selection, the method comprising receiving by a computing device, a location from a user device associated with a user; determining by the computing device, a plurality of nourishment possibilities within the location; locating by the computing device, a performance character associated with the user, wherein the performance character contains a nourishment score; generating by the computing device, a user profile wherein the user profile comprises the location, the plurality of nourishment possibilities, and the performance character; generating by the computing device, a selector machine-learning process, wherein the selector machine-learning process utilizes the user profile as an input, and outputs a plurality of corresponding nourishment possibility indexes; and grading by the computing device, the plurality of nourishment possibilities using the plurality of corresponding nourishment possibility indexes.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for geographically tracked nourishment selection. In an embodiment, a specified location is utilized to identify nourishment providers that provide service within the location. A user profile in combination with machine-learning processes are utilized to generate nourishment possibility indexes that reflect the effect of various nourishment possibilities on a user's nourishment score.

Figure 1:
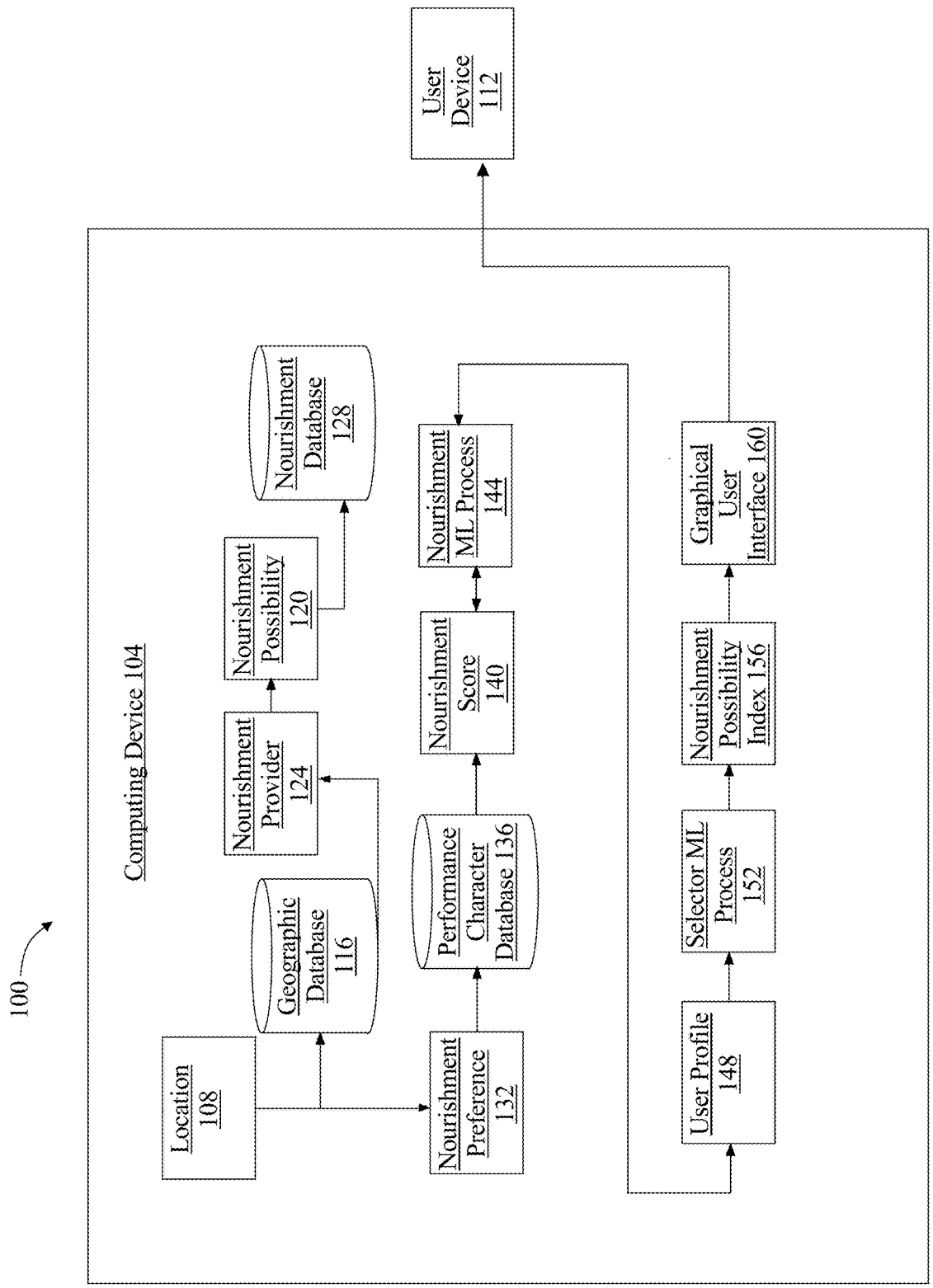
FIG. 1 is a block diagram illustrating an exemplary embodiment of a system for geographically tracked nourishment selection.

Referring now to FIG. 1, an exemplary embodiment of a system 100 for geographically tracked nourishment selection is illustrated. System 100 includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices 104 may be included together in a single computing device 104 or in two or more computing devices 104. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an association, a building, a campus or other relatively small geographic space), a telephone network, a data network associated with a telephone/voice provider (e.g., a mobile communications provider data and/or voice network), a direct connection between two computing devices 104, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices 104 in a first position and a second computing device 104 or cluster of computing devices 104 in a second position. Computing device 104 may include one or more computing devices 104 dedicated to data storage, security, dispersal of traffic for load balancing, and the like. Computing device 104 may distribute one or more computing tasks as described below across a plurality of computing devices 104 of computing device 104, which may operate in parallel, in series, redundantly, or in any other manner used for dispersal of tasks or memory between computing devices 104. Computing device 104 may be implemented using a "shared nothing" architecture in which data is cached at the operative, in an embodiment, this may enable scalability of system 100 and/or computing device 104.

Continuing to refer to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence recurrently until a desired or commanded outcome is achieved; repetition of a step or a sequence of steps may be performed iteratively and/or recursively using outputs of previous repetitions as inputs to subsequent repetitions, assembling inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, system 100 include a computing device 104 operating on computing device 104. Computing device 104 may be implemented as any hardware and/or software module. Computing device 104 is designed and configured to receive a location from a user device associated with a user; determine a plurality of nourishment possibilities within the location, locate a performance character associated with the user, wherein the performance character contains a nourishment score; generate a user profile wherein the user profile comprises the location, the plurality of nourishment possibilities, and the performance character; generate a selector machine-learning process, wherein the selector machine-learning process utilizes the user profile as an input, and outputs a plurality of corresponding nourishment possibility indexes; and grade the plurality of nourishment possibilities using the plurality of corresponding nourishment possibility indexes.

With continued reference to FIG. 1, a "location" as used in this disclosure, is a location that a user commutes to and/or from. A location may include a physical location such as the location of a user's home residence, workplace, grocery store where a user shops for groceries, eateries that a user enjoys dining at, sports stadium where a user watches baseball games and the like. A location 108 may specify a physical address of a location that a user may commute to and/or from. A location 108 may specify a town, county, state, and/or region that a user may commute to and/or from. A location 108 may specify a geographical region that a user may commute to and/or from such as the Northeast or Central Texas. A location may be commuted to by a user utilizing any mode of movement including for example by train, bus, car, airplane, taxicab, helicopter, boat, trolley, subway, metro, bicycle, scooter, moped, vehicle, on foot and the like. For instance and without limitation, a location 108 may specify that a user who resides in Dallas, Tex. intends to walk three blocks to a cafe on foot. In yet another non-limiting example, a location 108 may specify that a user intends to take a ferry between Bellingham, Wash., and Juneau, Ak. A location 108 may specify a particular time when a user intends to engage in a particular location 108. For example, a user may specify that the user intends to walk on foot from the user's household located on Sloane Street in Portland, Me., to the user's office located on Atlantic Street in Portland, Me., tomorrow morning at 9:00 am. A location 108 may specify a frequency of the location 108, such as if the user repeats a location on certain days of the week. For instance and without limitation, a user may visit the same consumers on the third Wednesday every quarter, whereby the user drives the same highways and/or roads to the visit the same consumers on the third Wednesday every quarter.

With continued reference to FIG. 1, a location 108 includes a practiced route containing a frequency character. A "practiced route," as used in this disclosure, is a location 108 that occurs with a particular frequency, and/or occurs by comparison to a preconfigured threshold. A practiced route may include a location 108 that a user engages in on specific days, such as a daily commute from a user's household to the user's office that occurs every Monday through Friday, excluding major holidays, vacations, and time off. A practiced route may include a location 108 that a user engages in on certain days each month. For example, a practiced route may include a trip to the hair salon on the third Friday of each month. A practiced route includes a frequency character, specifying the frequency of the practiced route. For example, a user may specify that the user stops at a local bakery before commuting to the user's job only on Friday mornings as a special treat to end the week. In yet another non-limiting example, a user may specify that the user takes a trip to the pharmacy on the last Saturday of each month to pick up a monthly standing prescription. A location 108 includes a multiple location route. A "multiple-location route," as used in this disclosure, is a location 108 that contains two or more locations that a user commutes to. For instance and without limitation, a multiple-location route may include a user who is commuting to the user's job, and then stopping to pick up dinner at an eatery on the way home. In yet another non-limiting example, a multiple-location route may include a user who is driving from Boise, Id., with a first stop in Idaho Falls, and a second stop in Billings, Mont. where the user will stay for three weeks, before returning and driving back home to Boise.

With continued reference to FIG. 1, computing device 104 receives a location from a user device associated with a user. A user device 112 may include without limitation, a display in communication with computing device 104, where a display may include any display as described herein. A user device 112 may include an additional computing device, such as a mobile device, laptop, desktop, computer, and the like. In an embodiment, a location 108 may be determined based on a global positioning system (GPS) of a user device 112. In such an instance, computing device 104 may receive an input from user device 112 specifying the latitude and longitude of a position where a user device 112 is currently located.

With continued reference to FIG. 1, information pertaining to a location 108 may be stored in geographic database 116. Geographic database 116 may be implemented, without limitation, as a relational database, a key-value retrieval datastore such has a NOSQL database, or any other format or structure for use as a datastore that a person skilled in the art would recognize as suitable upon review of the entirety of this disclosure.

With continued reference to FIG. 1, computing device 104 is configured to determine a plurality of nourishment possibilities within a location. A "nourishment possibility," as used in this disclosure, is any menu item available for sale and/or consumption by a nourishment provider. A nourishment possibility 120 may include dishes and/or meals offered on an actual menu created by a nourishment provider 124. For instance and without limitation, a nourishment provider 124 may offer three possible dinner options that a user can order and purchase, including fettucine alfredo, beef stew, or tofu and broccoli. A nourishment possibility may include meals and/or ingredients available for sale at a nourishment provider 124. For instance and without limitation, a nourishment possibility 120 may include a list of products available for purchase at a grocery store or a list of fresh produce that can be purchased at a farmer's market. A "nourishment provider," as used in this disclosure, is an establishment that provides food and/or beverages for sale and/or consumption. A nourishment provider 124 may include a restaurant, vending machine, grocery store, virtual store, meal delivery kit service, chef that sells meals and/or ingredients, café, food truck, bistro, fast food establishment, coffee house, pub, carry out only establishment, dine-in establishment, mixed carry out and/or dine in establishment, farm stand, market, farm and the like. A nourishment provider 124 provides nourishment possibilities.

With continued reference to FIG. 1, information pertaining to a nourishment provider 124 such as the physical address, hours of operation of a nourishment provider 124, menu options and the like may be stored in nourishment database 128. Nourishment database 128 may be implemented as any data structure suitable for use as geographic database 116 as described above in more detail. In an embodiment, computing device 104 may retrieve information pertaining to a particular nourishment provider 124 by generating a query. A "query" as used in this disclosure, is any information utilized to determine a nourishment possibility contained within nourishment database. Retrieval of a nourishment possibility 120 may be utilized as described below in more detail. For instance and without limitation, computing device 104 may utilize a user's location 108 to generate a query to determine a nourishment possibility 120 that can be delivered to the user based on the user's location 108. For instance and without limitation, computing device 104 may be provided with a location 108 from a user device 112 that specifies that a user will be traveling from the user's house to a local university where the user attends school. In such an instance, computing device 104 may generate a query to identify nourishment provider 124 situated near and/or that will deliver meals to the local university where the user attends school.

With continued reference to FIG. 1, computing device 104 is configured to determine a nourishment possibility using a nourishment preference 132. A "nourishment preference," as used in this disclosure, is a description of a user's likes and/or dislikes relating to nourishment possibilities. A nourishment preference 132 may specify food likes, food dislikes, ingredient likes, ingredient dislikes, food allergies, food intolerances, cuisine likes, cuisine dislikes, cooking method likes, cooking method dislikes, meal likes, meal dislikes, snack likes, snack dislikes, health goals, health objectives, meal time likes, meal time dislikes, eating patterns, eating habits, number of meals consumed each day, time of day of each meal consumed, food ingredient sources, food taste, and the like. Information pertaining to a user's nourishment preference 132 may be stored in geographic database 116. For instance and without limitation, a nourishment preference 132 may indicate that a user prefers foods that taste sweet, and foods that are sourced from organically grown ingredients. In yet another non-limiting example, a nourishment preference 132 may indicate that a user prefers not to consume any products containing eggs because the user dislikes the taste of eggs, and the user is allergic to sesame. Computing device 104 utilizes a nourishment preference 132 to generate a query to identify nourishment provider 124 that may comply with a nourishment preference 132. For instance and without limitation, a nourishment preference that specifies a user's allergy to shellfish may be utilized by computing device 104 to generate a query to locate nourishment provider 124 that provide nourishment possibilities that do not contain shellfish or that can be adapted and/or substituted to not contain shellfish.

With continued reference to FIG. 1, computing device 104 is configured to determine a nourishment possibility using a logged user performance metric. A "logged user performance metric," as used in this disclosure, is a description of any previously consumed nourishment possibility 120. A logged user performance metric may include a description of a meal that a user ate, a series of meals, and the like. One or more logged user performance metrics may be stored within geographic database 116. A logged user performance metric may contain a timestamp, indicating the date and time when a user consumed a logged user performance metric. A logged user performance metric may include any extra information about a meal, such as any methods of preparing the meal, any ways in which the meal was customized to the user's preferences, how well the user liked or disliked the meal, and/or what serving size of the meal the user consumed. Computing device 104 may utilize a logged user performance metric to locate nourishment provider 124 that offer meals similar to what the user ate. For instance and without limitation, a logged user performance metric that specifies that a user consumes bacon and eggs for breakfast every morning may be utilized to locate a nourishment provider 124 that offers bacon and eggs when the user is traveling for work. In yet another non-limiting example, a logged user performance metric that specifies that a user consumed a Rueben sandwich and the user did not like the Rueben sandwich may be utilized to eliminate a nourishment provider 124 that offers only Rueben sandwiches for lunch.

With continued reference to FIG. 1, computing device 104 is configured to locate a performance character associated with a user. A "performance character," as used in this disclosure, is a behavior that influences selection of a nourishment provider 124 and/or consumption of a nourishment possibility 120. A behavior may include any repeated pattern of activity and/or habits that a user performs. A behavior may include any behaviors relating to nourishment possibilities, such as eating habits that contain a log of one or more previously consumed meals. For instance and without limitation, a behavior may include a series of logged meals that a user consumed over the past week, that specify that a user consumed oatmeal for breakfast every morning. In yet another non-limiting example, a behavior may include a series of logged meals that a user consumed over the past month which indicate that the user consumed all organic ingredients and all products were vegan and did not contain any animal products. A behavior may include any fitness behaviors, including any exercise habits that may influence meals and/or ingredients that a user consumes. For instance and without limitation, a user who is training to run a marathon may consume a diet containing a higher percentage of carbohydrates as compared to when the user is not training to run a marathon. A behavior may include a style of eating, such as a user who follows a "meatless Monday" approach and does not consume meat on Mondays. A behavior may include a description of a user's style of eating or eating habits, such as a user who engages in intermittent fasting, and who does not consume meals any time outside of 9 am-5 pm each day. One or more logged user performance metrics may be stored within a performance character database 136. Performance character database 136 may be implemented as any data structure suitable for use as geographic database 116 as described above in more detail.

With continued reference to FIG. 1, a performance character contains a nourishment score 140. A "nourishment score," as used in this disclosure, is data, including any character, symbolic, and/or numerical data, reflecting the current nutritional state of a user. A nourishment score 140 may be transient and/or dynamic. A nourishment score 140 may be updated based on one or more meals that a user consumed and/or is planning to consume. A nourishment score 140 may be calculated by computing device 104 by retrieving information contained within performance character database 136. A nourishment score 140 may be graded on a continuum, where a score of zero may indicate a user who is in extremely poor nutritional health while a score of 100 may indicate a user who is in excellent nutritional health. A nourishment score 140 may be calculated from one or more factors that may be stored within performance character database 136 such as food intake, water intake, supplement intake, prescription medication intake, fitness practice, health goals, chronic health conditions, acute health conditions, spiritual wellness, meditation practice, stress levels, and the like.

With continued reference to FIG. 1, computing device 104 is configured to calculate a nourishment score 140 using a machine-learning process. Computing device 104 retrieves an element of data containing a logged nourishment entry. A "logged nourishment entry," as used in this disclosure, is any stored factor that is utilized to calculate a nourishment score 140. A logged nourishment entry may include a user's daily water intake, a user's supplement intake, and the like as described below in more detail. A logged nourishment entry may include a nourishment behavioral target. A "nourishment behavioral target," as used in this disclosure, is a user behavior goal relating to nourishment possibilities. A behavior goal may include a desire to cook a certain number of meals at home each week, or a desire to only eat fast food a certain number of times each month. A behavior goal may be self-reported by a user, and a user's progress towards meeting the behavior goal may be calculated into a user's nourishment score 140. For example, a user who continues to not achieve any progress towards a user's nourishment behavior target to eat fish at least three times each week may decrease a user's overall nourishment score 140, while a user with the same nourishment behavior target and who does continuously eat fish three times each week may increase the user's overall nourishment score 140. A behavior goal may relate to a food source, such as a desire to only go out to eat no more than three days each week and to eat the rest of a user's meals at home. A behavior goal may relate to a food option such as to only consume foods that do not contain genetically modified organisms, or to only consume foods that do not contain high fructose corn syrup.

One or more logged nourishment entries may be stored with performance character database 136. Computing device 104 may retrieve one or more elements of data containing a logged nourishment entry such as by generating a query, including any of the queries as described herein. Computing device 104 generates a nourishment machine-learning process 144. A "machine-learning process," as used in this disclosure, is a process that automatically uses a body of data known as "training data" and/or a "training set" to generate an algorithm that will be performed by computing device 104 and/or a module to produce outputs given data provided as inputs; this is in contrast to a non-machine learning software program where the commands to be executed are determined in advance by a user and written in a programming language. A "nourishment machine-learning process," as used in this disclosure, is any machine-learning process that utilizes a logged nourishment entry as an input, and outputs a nourishment score 140. Nourishment machine-learning process 144 is trained using a first training set relating logged nourishment entries to nourishment score 140. "Training data," as used in this disclosure, is data containing correlations that a machine-learning process including a machine-learning algorithm and/or machine-learning process may use to model relationships between two or more categories of data elements. Training data may be formatted to include labels, for instance by associating data elements with one or more descriptors corresponding to categories of data elements. Training data may not contain labels, where training data may not be formatted to include labels. Nourishment machine-learning process may be generated calculating one or more machine-learning algorithms and/or producing one or more machine-learning models.

With continued reference to FIG. 1, a machine-learning process may include one or more supervised machine-learning algorithms, which may include active learning, classification, regression, analytical learning, artificial neural network, backpropagation, boosting, Bayesian statistics, case-based learning, genetic programming, Kernel estimators, naïve Bayes classifiers, maximum entropy classifier, conditional random field, K-nearest neighbor algorithm, support vector machine, random forest, ordinal classification, data pre-processing, statistical relational learning, and the like. A machine-learning algorithm may include an unsupervised machine-learning algorithm, that is trained using training data that does not contain data labels. An unsupervised machine-learning algorithm may include a clustering algorithm such as hierarchical clustering, k-means clustering, mixture models, density based spatial clustering of algorithms with noise (DBSCAN), ordering points to identify the clustering structure (OPTICS), anomaly detection such as local outlier factor, neural networks such as autoencoders, deep belief nets, Hebbian learning, generative adversarial networks, self-organizing map, and the like. A machine-learning algorithm may include semi-supervised learning that may be trained using training data that contains a mixture of labeled and unlabeled data. A machine-learning algorithm may include reinforcement learning, self-learning, feature learning, sparse dictionary learning, anomaly detection, robot learning, association rules, and the like. A machine-learning algorithm may include generating one or more machine-learning models. A "machine-learning model," as used in this disclosure, is any mathematical representation of a relationship between inputs and outputs. A machine-learning model an artificial neural network, a decision tree, a support vector machine, regression analysis, Bayesian network, genetic algorithms, and the like.

With continued reference to FIG. 1, computing device 104 is configured to generate a user profile 148. A "user profile," as used in this disclosure, is a compilation of one or more elements of data pertaining to a user. A user profile 148 may include any information pertaining to a user that may be stored in geographic database 116, nourishment database 128 and/or performance character database 136. A user profile 148 includes a location 108, a plurality of nourishment possibilities 120, and a performance character. Computing device 104 is configured to generate a user profile 148 utilizing user metric data. Computing device 104 is configured to retrieve an element of user metric data. An "element of user metric data," as used in this disclosure, is data describing a user's logistical preferences. Logistical preferences may include any information describing how much money a user is looking to spend on a nourishment possibility, preferred grocery store and/or restaurants, style of eating, if the user is looking to prepare a meal or acquire an already prepared meal, if the user will pick up the meal from the nourishment provider 124 or if the user will order the nourishment possibility 120 to be delivered to the user, how soon the user is looking to consume the nourishment possibility 120, ingredient grade of the ingredients contained within the nourishment possibility 120, and the like. Information pertaining to an element of user metric data may be stored within performance character database 136. Computing device 104 generates a user profile 148 containing user metric data.

With continued reference to FIG. 1, computing device 104 is configured to generate a selector machine-learning process 152. A "selector machine-learning process" is a machine-learning process that utilizes a user profile 148 as an input and outputs corresponding nourishment possibility indexes. Selector machine-learning process 152 may be implemented as any machine-learning process as described herein. Selector machine-learning process 152 is trained using a second training set relating user profile 148 to nourishment possibility indexes 156. A second training set may be obtained from previous iterations of generating selector machine-learning process 152, user entries, and/or expert input. A "nourishment possibility index," as used in this disclosure, is a description of the impact of a nourishment possibility 120 on a user's body. A nourishment possibility index 156 may contain an indication as to whether a nourishment possibility 120 may positively or negatively impact a nourishment score 140. For instance and without limitation, a nourishment possibility 120 that contains a snack consisting of a flavored ice coffee and a slice of pound cake as negatively impacting a nourishment score 140 that indicates the user is in a depleted nutritional state. In yet another non-limiting example, a nourishment possibility 120 that contains a breakfast option consisting of bacon, eggs, and sausage may indicate that it will have a positive impact on a nourishment score 140 for a user who is in a protein deficient state and needs to rebuild depleted protein stores. A nourishment possibility index 156 may contain information detailing how much a nourishment possibility 120 may affect a nourishment score 140. For instance and without limitation, a nourishment possibility 120 that contains fried chicken served with French fries and coleslaw may impact a nourishment score 140 by decreasing it by ten points, while a nourishment possibility 120 that contains pan seared salmon served on a bed of sautéed spinach and mushrooms may increase a nourishment score 140 by six points. Computing device 104 may calculate and determine the effect of a nourishment possibility 120 on a nourishment possibility 120 score utilizing information contained within nourishment database 128.

With continued reference to FIG. 1, computing device 104 is configured to grade corresponding nourishment possibilities using nourishment possibility indexes 156. Grading may include ranking nourishment possibilities on a scale based on which nourishment possibilities will positively impact a nourishment score 140, which nourishment possibilities will have a neutral impact on a nourishment score 140, and which nourishment possibilities will negatively impact a nourishment score 140.

With continued reference to FIG. 1, computing device 104 is configured to display graded corresponding nourishment possibilities on computing device 104. Computing device 104 may contain a graphical user interface 160 configured to display graded corresponding nourishment possibilities. Graphical user interface 160 may include without limitation, a form or other graphical element having display fields, where one or more elements of information may be displayed. Graphical user interface 160 may include sliders that may reflect how compatible a nourishment possibility 120 is for a user based on a user's nourishment score 140. Graphical user interface 160 may contain free form textual entries, where a user may be able to type in information. Computing device 104 receives a user selection selecting a corresponding nourishment possibility 120. A "user selection," as used in this disclosure, is any user command selecting one or more nourishment possibilities. A user may select a nourishment possibility 120 such as by using a slider located on graphical user interface 160 to select a particular nourishment possibility 120. A user may select a nourishment possibility 120 such as by typing an entry into a free form textual entry containing a command of what a nourishment possibility 120 a user wishes to order. Computing device 104 logs a user entry. Computing device 104 may log a user entry, such as by incorporating a user entry into a memory located within computing device 104. A user entry contains a user preference for a user selection. A "user preference for a user selection," as used in this disclosure, is any review of a nourishment possibility 120 after a user consumed the nourishment possibility 120. A user preference for a user selection may indicate how well a user tolerated a nourishment possibility 120, if a user enjoyed eating the nourishment possibility 120, what the user liked about the nourishment possibility 120, what the user disliked about the nourishment possibility 120, if the user had a reaction to the nourishment possibility 120, and the like. Computing device 104 incorporates a user selection and a user preference for the user selection into selector machine-learning process 152. For example, a user selection and/or a user preference for the user selection process may be utilized as subsequent training data, and/or incorporated into a selector machine-learning algorithm and/or a selector machine learning process.

With continued reference to FIG. 1, computing device 104 is configured to receive an input containing a request for a group location. A "group location," as used in this disclosure, any location 108 where two or more users are present. A group location may include a family who reside at the same house, or an office with fifty employees. In an embodiment, a user may enter a location 108 and specify a group location contained within the location 108. Computing device 104 combines group nourishment possibility indexes 156 for a group location. Combining may include storing group nourishment possibility indexes 156 together in memory or storing them together in a database located on computing device 104. Such information may be utilized to receive a user selection and coordinate delivery of the user selection to the group location. For instance and without limitation, an office may wish to order lunch for all of its employees during a meeting. In such an instance, computing device 104 may receive a location 108 from each of the employees specifying the group location. Computing device 104 calculates nourishment possibility indexes 156 for each of the employees and combines group nourishment possibility indexes 156 for the group location. Such information may then be utilized to deliver and/or transport selected nourishment possibilities to the group location.

Figure 2:
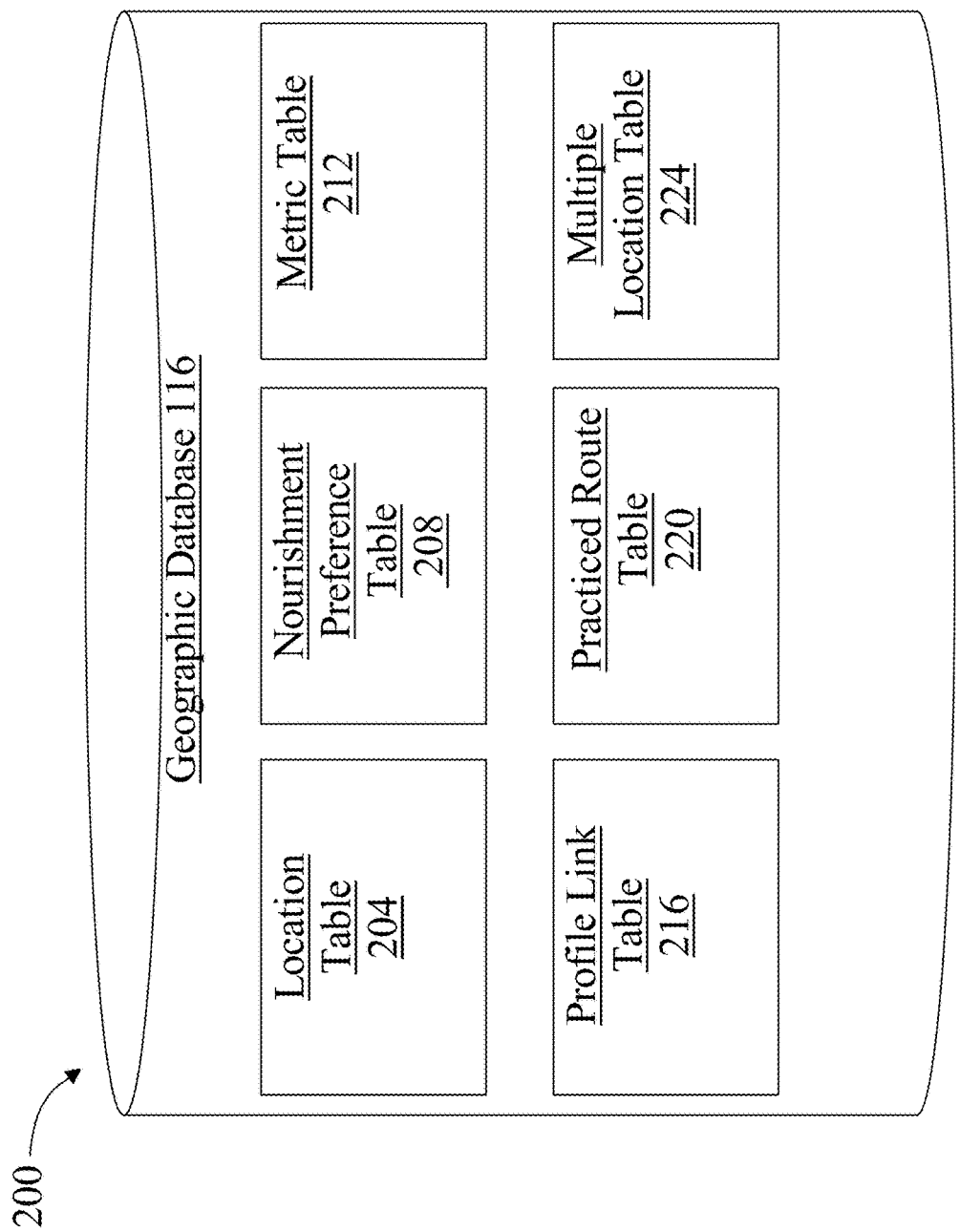
FIG. 2 is a block diagram illustrating an exemplary embodiment of a geographic database.

Referring now to FIG. 2, an exemplary embodiment 200 of geographic database 116 is illustrated. Geographic database 116 may be implemented as any data structure as described above in more detail in reference to FIG. 1. One or more tables contained within geographic database 116 may include location table 204; location table 204 may include information describing one or more location 108. For instance and without limitation, location table 204 may contain information describing a route user takes daily during the week to travel from home to the user's work and back home again. One or more tables contained within geographic database 116 may include nourishment preference table 208; nourishment preference table 208 may include information pertaining to a user's nourishment preference 132. For instance and without limitation, nourishment preference table 208 may include information specifying a user's preference for salty foods, and foods that do not contain genetically modified organisms. One or more tables contained within geographic database 116 may include metric table 212; metric table 212 may include one or more user performance metrics, including any of the user performance metrics as described above in more detail in reference to FIG. 1. For instance and without limitation, metric table 212 may include information a description of a dinner option that a user consumed that consisted of grilled swordfish served on a bed of basmati rice with a mango salsa. One or more tables contained within geographic database 116 may include profile link table 216; profile link table 216 may link information contained within geographic database 116 to information that will be utilized to generate a user profile 148. One or more tables contained within geographic database 116 may include practiced route table 220; practiced route table 220 may include information describing one or more practiced routes. For instance and without limitation, practiced route table 220 may contain an entry describing a route a user travels every Saturday morning from a user's house to a gym located one town away to attend a fitness class. One or more tables contained within geographic database 116 may include multiple location table 224; multiple location table 224 may include location 108 containing multiple locations. For instance and without limitation, multiple location table 224 may contain information describing a user's travels that include a trip starting at a user's office building, to a first stop at a local pharmacy and a second stop at a grocery store.

Figure 3:
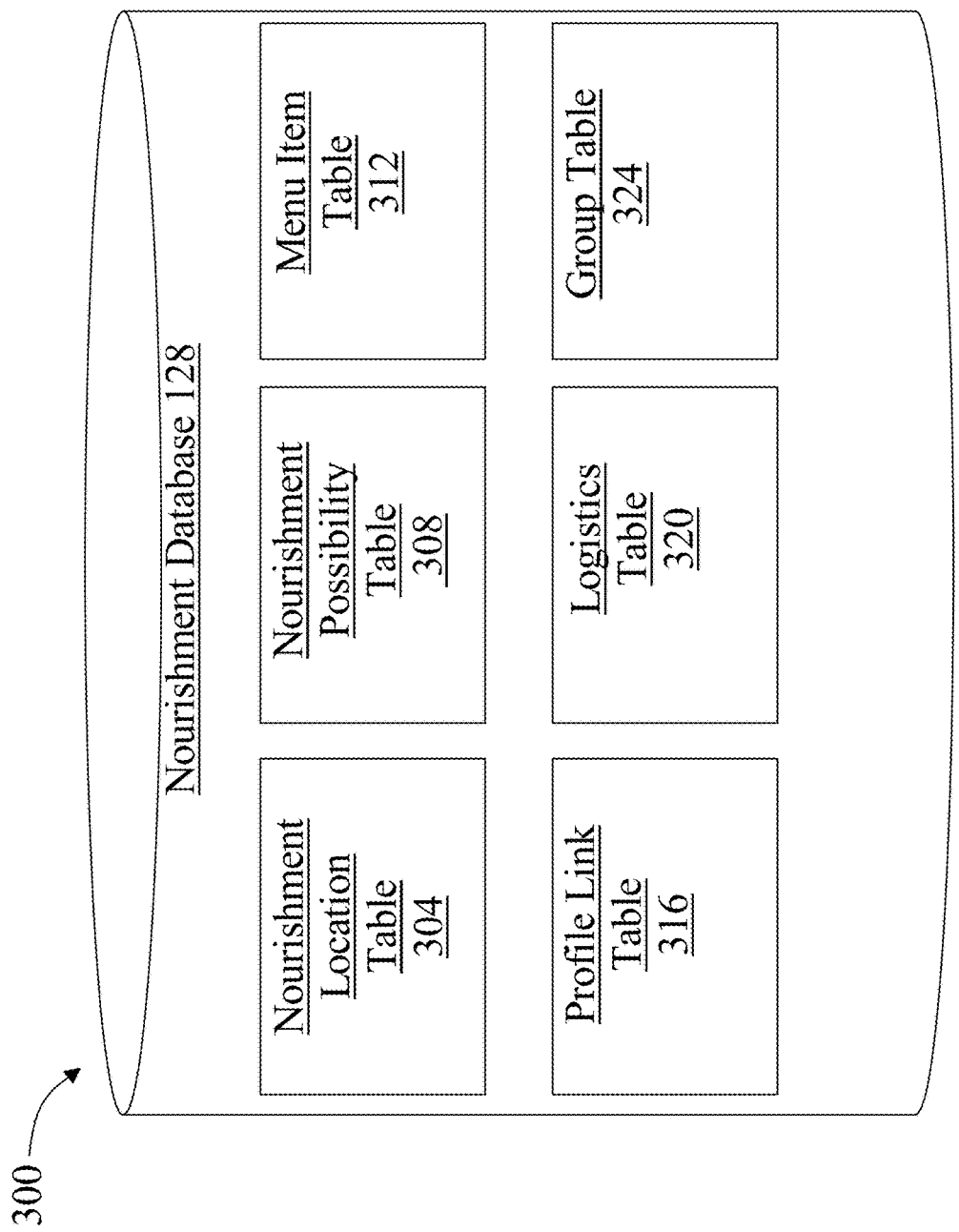
FIG. 3 is a block diagram illustrating an exemplary embodiment of a nourishment database.

Referring now to FIG. 3, an exemplary embodiment 300 of nourishment database 128 is illustrated. Nourishment database 128 may be implemented as any data structure suitable for use as described above in more detail in reference to FIG. 1. One or more tables contained within nourishment database 128 may include nourishment provider table 304; nourishment provider table 304 may include information describing pertinent logistical information relating to a nourishment provider 124. For instance and without limitation, nourishment provider table 304 may include information describing the address of a nourishment provider 124, hours of operation, pick up, take out, and/or delivery options, cuisine type, and the like. One or more tables contained within nourishment database 128 may include nourishment possibility table 308; nourishment possibility table 308 may contain information describing nourishment possibilities offered by one or more nourishment provider 124. For instance and without limitation, nourishment possibility table 308 may contain information describing various lunch options available to order from a nourishment provider 124. One or more tables contained within nourishment database 128 may include menu item table 312; menu item table 312 may include information describing menu items offered by one or more nourishment provider 124. For instance and without limitation, menu item table 312 may contain information describing various seasonal items available to purchase at a coffee shop, such as a gingerbread latte during the winter months. One or more tables contained within nourishment database 128 may include profile link table 316; profile link table 316 may link information contained within nourishment database 128 that will be used to generate a user profile 148. One or more tables contained within nourishment database 128 may include logistics table 320; logistics table 320 may information relating to logistical considerations to order and/or purchase nourishment possibilities from a nourishment provider 124. For instance and without limitation, logistics table 320 may include information describing food substitutions and/or modifications that can be accommodated, such as a request to prepare a vegan meal option or to make an entrée dairy free. One or more tables contained within nourishment database 128 may include group table 324; group table 324 may include information pertaining to group ordering from a nourishment provider 124. For instance and without limitation, group table 324 may include information pertaining to meal options and/or menu items available for groups.

Figure 4:
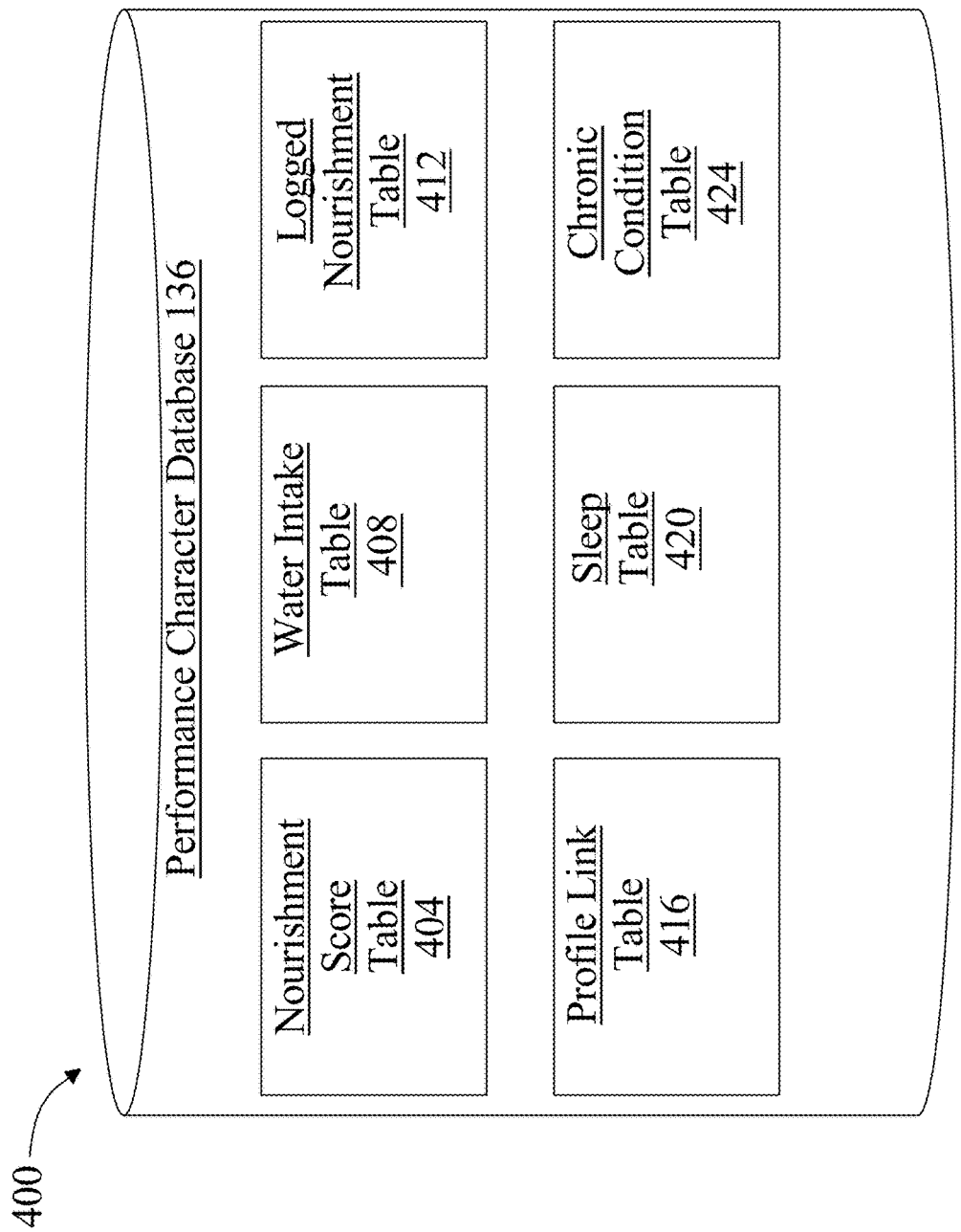
FIG. 4 is a block diagram illustrating an exemplary embodiment of a performance character database.

Referring now to FIG. 4, an exemplary embodiment of performance character database 136 is illustrated. Performance character database 136 may be implemented as any data structure suitable for use as described above in more detail in reference to FIG. 1. One or more tables contained within performance character database 136 may include nourishment score table 404; nourishment score table 404 may include information describing a user's nourishment score 140. For instance and without limitation, nourishment score table 404 may contain a nourishment score 140 calculated for a user utilizing a series of previously consumed meals that a user ate. One or more tables contained within performance character database 136 may include water intake table 408; water intake table 408 may contain a log of how much water a user is drinking on a daily basis. For instance and without limitation, water intake table 408 may contain an entry specifying that a user consumed 2.5 liters of water the previous day. One or more tables contained within performance character database 136 may include logged nourishment table 412; logged nourishment table 412 may include information describing one or more logged nourishment entries. For instance and without limitation, logged nourishment table 412 may include information describing one or more factors that may be utilized to calculate a user's nourishment score 140, such as how many alcoholic beverages they consumed over the course of the past 7 days. One or more tables contained within performance character database 136 may include profile link table 416; profile link table 416 may link information contained within performance character database 136 that will be used to generate a user profile 148. One or more tables contained within performance character database 136 may include sleep table 420; sleep table 420 may include information describing a user's sleep patterns. For instance and without limitation, sleep table 420 may contain entries detailing how much sleep a user gets each night. One or more tables contained within performance character database 136 may include chronic condition table 424; chronic condition table 424 may include information relating to any chronic medical conditions that a user has been diagnosed with and/or suffers from. For instance and without limitation, chronic condition table 424 may include an entry specifying that a user suffers from multiple sclerosis and has been taking a medication to help keep it under control.

Figure 5:
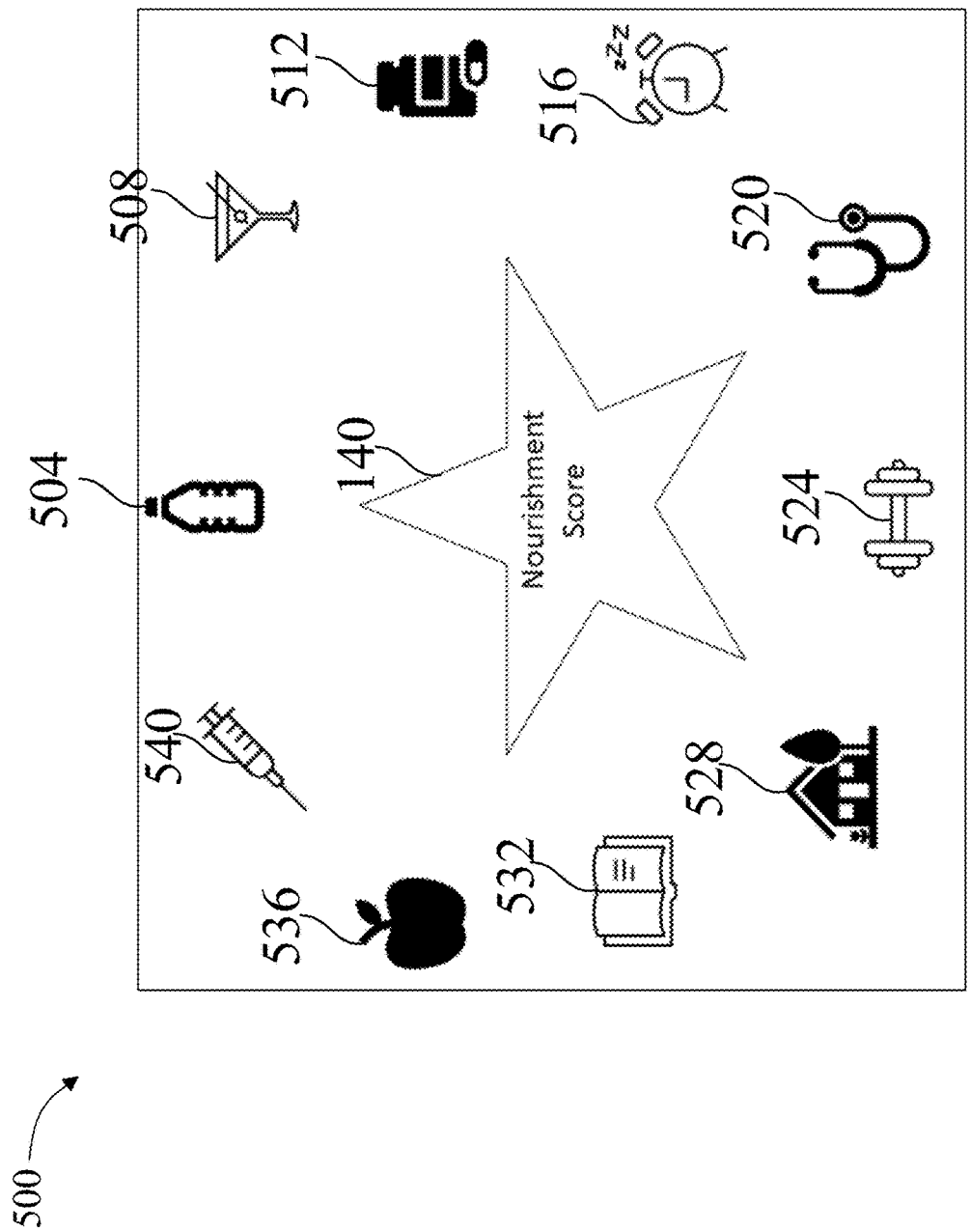
FIG. 5 is a diagrammatic representation of an exemplary embodiment of a nourishment score.

Referring now to FIG. 5, an exemplary embodiment of factors utilized to calculate a nourishment score 140 are illustrated. One or more factors may be stored within performance character database 136 as described above in more detail in reference to FIG. 1. Information pertaining to one or more factors may be received utilizing inputs received from user device 112. In an embodiment, a user may be presented with a series of questions that may prompt a user for a response. For example, computing device 104 may ask a user how many alcoholic drinks the user consumed over the course of the previous day or week. Such information may be gathered and stored within performance character database 136. In an embodiment, information relating to one or more factors may be logged by a user and stored within memory of computing device 104. For example, a user may provide daily or weekly updates relating to certain factors such as how many alcoholic drinks the user had the night before, or what meals the user ate the previous day. Computing device 104 calculates a nourishment score 140 utilizing any of the methods as described above in more detail in reference to FIG. 1. One or more factors utilized to calculate a nourishment score 140 may include water consumption 504. For example, a user may provide information detailing how much water the user consumed over the course of the previous day. One or more factors utilized to calculate a nourishment score may include alcoholic beverage consumption 508. For example, a user may provide information detailing how many alcoholic drinks they consumed during the previous week, or how many alcoholic drinks they consume on average each week. One or more factors utilized to calculate a nourishment score 140 may include medication use 512. Medication use 512 may include any information pertaining to any prescription medications, over the counter medications, and/or supplement medications that a user may be taking. One or more factors utilized to calculate a nourishment score 140 may include sleep factor 516; sleep factor 516 may include any information pertaining to a user's sleep patterns. For example, sleep factor 516 may contain information such as how much sleep a user gets each night, problems with falling asleep, problems with staying asleep, nighttime sleep behaviors and the like. One or more factors utilized to calculate a nourishment score 140 may include physical health factor 520. Physical health factor 520 may include information describing any chronic medical problems, acute medical problems, diagnoses, and the like that the user may be suffering from, recovered from, and/or currently treating. One or more factors utilized to calculate a nourishment score 140 may include fitness factor 524. Fitness factor 524 may include information describing fitness routines and/or any physical fitness that a user performs. One or more factors utilized to calculate a nourishment score 140 may include personal life factor 528. Personal life factor 528 may include information describing any personal information pertaining to a user, such as a user's marital status, socioeconomic status, employment history, number of children, education, and the like. One or more factors utilized to calculate a nourishment score 140 may include spiritual factor 532. Spiritual factor 532 may include information describing a user's spiritual practice and/or spiritual beliefs. For example, spiritual factor 532 may include information describing a user's Christian beliefs and may include information detailing that a user regularly attends a bible study class every Wednesday night. One or more factors utilized to calculate a nourishment score 140 may include nutritional factor 536. Nutritional factor 536 may include information describing a user's nutritional, dietary, and/or styles of eating. One or more factors utilized to calculate a nourishment score 140 may include a medical procedures factor 540. Medical procedures factor 540 may include information describing any previous, current, and/or future medical procedures and/or surgeries that a user has had or may require.

Figure 6:
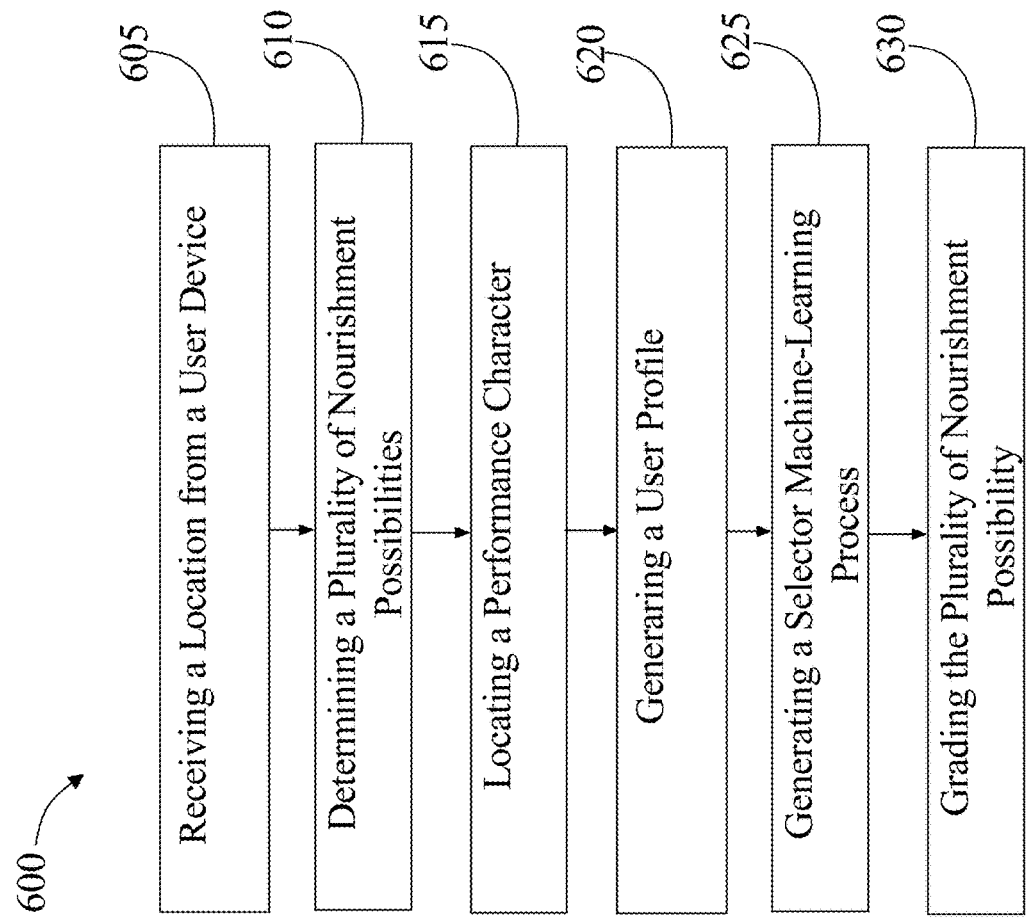
FIG. 6 is a process flow diagram illustrating an exemplary embodiment of a method of geographically tracked nourishment selection.

Referring now to FIG. 6, an exemplary embodiment of a method 600 of geographically tracked nourishment selection is illustrated. At step 605, computing device 104 receives a location from a user device associated with a user. Computing device 104 receives a location 108 from a user device 112 utilizing any network methodology as described herein. A location 108 includes any of the location 108 as described above in more detail. A location 108 specifies a location that a user travel to and/or from. For instance and without limitation, a location 108 may describe a location such as traveling from a user's work to a pharmacy to pick up a prescription. In yet another non-limiting example, a location 108 may describe a location such as traveling from a user's work the house of a relative to have dinner together. A location 108 my specify a practiced route containing a frequency character, such as a route that a user may take repeatedly or on multiple occasions. For example, a practiced route may include a location a user travels such as from the user's house to a dance studio every Monday and Friday morning to participate in a dance class. A practiced route contains a frequency character, specifying how many times the user travels on the practiced route. For example, a practiced route may specify that a user travels the practiced route once per week, only on the weekends, only during business hours, the second Monday each month and the like. A location 108 may include a multiple location route. A multiple location route includes any of the multiple location routes as described above in more detail in reference to FIG. 1. For instance and without limitation, a multiple location route may specify that a user will be traveling from a grocery store to a dry cleaner's then to a gym and then back to the user's house. One or more location 108 pertaining to a user may be stored in geographic database 116 as described above in more detail in reference to FIG. 1.

With continued reference to FIG. 6, at step 610, computing device 104 determines a plurality of nourishment possibilities within a location. A nourishment possibility 120 includes any menu item available for sale and/or consumption by a nourishment provider 124. For example, a nourishment possibility 120 may include a ginger flavored kombucha available for sale at a juice bar or a dinner entrée of gluten free eggplant parmesan served with a side salad and gluten free pasta available at an Italian restaurant. Information pertaining to the location of a nourishment provider 124 may be stored in nourishment database 128 as described above in more detail in reference to FIG. 1. A nourishment provider 124 includes any of the nourishment provider 124 as described above in more detail in reference to FIG. 1. A nourishment provider 124 includes any establishment that provides food and/or beverages for sale and/or consumption. For instance and without limitation, a nourishment provider 124 may include a supermarket, a restaurant, a food truck, a café, a coffee shop, a cafeteria, a food hall, a smoothie bar, and the like. A nourishment provider 124 provides nourishment possibilities. A nourishment possibility 120 includes any of the nourishment possibilities as described above in more detail in reference to FIG. 1. Computing device 104 locates a nourishment provider 124, such as by utilizing a location to generate a search query, to locate nourishment provider 124 located near the location. A query includes any of the queries as described above in more detail in reference to FIG. 1. For instance and without limitation, a location may contain a location such as a trip from a user's workplace located in Dallas, Tex., to a sporting event for the user's son located in Fort Worth, Tex. In such an instance, computing device 104 may utilize the location to generate a query to locate nourishment provider 124 located along the route between Dallas and Fort Worth.

With continued reference to FIG. 6, computing device 104 determines a plurality of nourishment possibilities utilizing information supplied by and/or pertaining to a user. Computing device 104 locates a nourishment possibility 120 utilizing a nourishment preference 132. A nourishment preference 132 contains a description of a user's likes and/or dislikes relating to nourishment possibilities, such as cuisines the user likes or dislikes, ingredients the user likes or dislikes, food tastes the user likes or dislikes, cooking styles the user likes or dislikes, and the like. Information pertaining to a nourishment preference 132 may be stored in geographic database 116 as described above in more detail in reference to FIGS. 1-2. Computing device 104 may utilize information pertaining to a nourishment preference 132 to locate nourishment provider 124 that offer nourishment possibilities that match a user's nourishment preference 132, and/or to eliminate nourishment provider 124 that do not match the user's nourishment preference 132. For instance and without limitation, nourishment preference 132 may specify that a user likes sweet tasting foods, and dislikes salty foods. In such an instance, computing device 104 may locate nourishment provider 124 that offer sweet foods such as a coffee shop, or a bakery, and eliminate nourishment provider 124 that offer salty foods, such as a restaurant that is famous for serving fish and chips. Computing device 104 locates a plurality of nourishment possibilities utilizing a logged user performance metric. A logged user performance metric includes any of the logged user performance metrics as described above in more detail in reference to FIG. 1. A logged user performance metric may contain any previously consumed nourishment possibilities that a user ate. For example, a logged user performance metric may contain a record of a series of meals that a user ate over the course of the prior week or month for instance. Computing device 104 may examine logged user performance metrics to identify eating habits and/or trends of a user and utilize the identified eating habits and/or trends to locate nourishment provider 124 that serve similar foods or meal options. For example, a logged user performance metric may identify that a user routinely eats Asian inspired meals, and computing device 104 may utilize this information to locate nourishment provider 124 that offer Asian inspired nourishment possibilities.

With continued reference to FIG. 6, at step 615, computing device 104 locates a performance character associated with a user, wherein the performance character contains a nourishment score. A performance character includes any behavior that may influence determining a plurality of nourishment possibilities. For instance and without limitation, a performance character may include any eating habits a user has, such as if a user skips breakfast and only eats lunch or dinner. A performance character may include any diets or ways of eating that a user follows, such as a user who follows intermittent fasting, and only eats within the hours between 12 pm and 6 pm each day. One or more performance characters may be stored within performance character database 136, as described above in more detail in reference to FIGS. 1-4. A performance character relating to a user includes a nourishment score 140, including any of the nourishment score 140 as described above in more detail in reference to FIG. 1. A nourishment score 140 reflecting the current nutritional state of a user. A nourishment score 140 may be calculated utilizing one or more factors, as described above in more detail in reference to FIG. 5. A factor may include for example, how much sleep a user gets each night, or how much water a user drinks each day. Computing device 104 may determine a nutritional score for a user by consulting information stored within performance character database 136. Computing device 104 may determine a nutritional score for a user by retrieving an element of data containing a logged nourishment entry. Information pertaining to a logged nourishment entry may be stored within performance character database 136. A logged nourishment entry contains information relating to any factor, including any of the factors as described above in more detail in reference to FIG. 5. For example, a logged nourishment entry may specify a user's workout routine over the course of the prior month, or what type of spiritual practice the user engages in. In an embodiment, a performance character includes a nourishment behavioral target. A nourishment behavior target includes any of the nourishment behavioral targets as described above in more detail in reference to FIGS. 1-5. For example, a nourishment behavior target may contain a goal or desired nourishment state of a user, such as a goal to eat a vegetarian diet or a goal to not eat any processed foods. Information pertaining to a nourishment behavior target may be utilized to calculate and/or determine a nourishment score 140. Such information may be stored within geographic database 116. Computing device 104 generates a nourishment machine-learning process 144, that utilizes a logged nourishment entry as an input, and outputs a nourishment score 140. Nourishment machine-learning process 144 includes any of the nourishment machine-learning process 144*es* as described above in more detail in reference to FIG. 1. For example, a nourishment machine-learning process 144 may include an unsupervised machine-learning algorithm, such as a k-nearest neighbor algorithm. Nourishment machine-learning process 144 may be trained using a first training set relating logged nourishment entries to nourishment score 140.

With continued reference to FIG. 6, at step 620, computing device 104 generates a user profile 148. A user profile 148 includes any of the user profile 148 as described above in more detail in reference to FIG. 1. A user profile 148 may contain one or more data entries pertaining to a user. A user profile 148 includes a location 108, a plurality of nourishment possibilities, and a performance character. Computing device 104 may generate a user profile 148 utilizing an element of user metric data. User metric data may contain information pertaining to a user's logistical preferences regarding nourishment possibilities and/or nourishment provider 124. For example, user metric data may specify how much money a user is willing to spend on a nourishment possibility 120, what time of the day a user prefers to eat certain meals at, if a user is looking to be waited on at a restaurant, cook a meal at home, have a meal delivered to a particular location, and the like. Computing device 104 generates a user profile 148 utilizing an element of user metric data.

With continued reference to FIG. 6, at step 625, computing device 104 generates a selector machine-learning process 152. Selector machine-learning process 152 includes any of the selector machine-learning process 152 as described above in more detail in reference to FIG. 1. Selector machine-learning process 152 utilizes a user profile 148 as an input, and outputs corresponding nourishment possibility indexes 156. Selector machine-learning process 152 is trained utilizing second training set relating user profile 148 to nourishment possibility indexes 156. Selector machine-learning process 152 may be implemented as any machine-learning process as described above in more detail in reference to FIGS. 1-5. A nourishment possibility index 156 contains a description of the impact of a nourishment possibility 120 on a user's body and/or nourishment score 140. A nourishment possibility index 156 may contain an impact of a plurality of nourishment possibilities from a plurality of nourishment providers 124. For instance and without limitation, a nourishment possibility index 156 may contain an indication as to how a nourishment possibility 120 may negatively, positively, and/or neutrally impact a nourishment score 140. For instance and without limitation, a nourishment possibility 120 such as fried fish and chips may neutrally impact a nourishment score 140 for a user who has been eating clean for several weeks, while a nourishment possibility 120 such as fettuccine alfredo may negatively impact a nourishment score 140 for a user who has not been eating clean for several weeks. In yet another non-limiting example, a nourishment possibility 120 such as a breakfast option of fresh fruit and yogurt may more positively impact a nourishment score 140 as compared to a breakfast option of bacon, sausage, and an omelet made with full fat cheese. A nourishment possibility index may contain a description of an impact on a nourishment score 140 on a continuum, and/or may contain a numerical score indicating exactly how a nourishment possibility 120 will impact the nourishment score 140.

With continued reference to FIG. 6, at step 630, computing device 104 grades a plurality of nourishment possibilities using nourishment possibility indexes 156. Grading may include organizing and/or ranking nourishment possibilities, according to which nourishment possibilities will have a positive impact on a user's health and/or nourishment score 140, which nourishment possibilities will have a negative impact on a user's health and/or nourishment score 140, and which nourishment possibilities will have a neutral impact on a user's health and/or nourishment score. In an embodiment, computing device 104 may grade nourishment possibilities on a scaled continuum. Computing device 104 may generate contextual descriptions, that may describe future health effects of a nourishment possibility 120 on a nourishment score 140. For instance and without limitation, a nourishment possibility index 156 linked to a nourishment possibility 120 such as fried chicken and waffles may contain a contextual description that the nourishment possibility 120 will have a negative impact on a user's nourishment score 140, but that removing the fried chicken from the waffle will result in the nourishment possibility 120 have a neutral impact on the user's nourishment score 140.

With continued reference to FIG. 6, computing device 104 displays graded corresponding nourishment possibilities on computing device 104, such as through a graphical user interface 160 as described above in more detail in reference to FIG. 1. Computing device 104 receives a user selection selecting a first nourishment possibility 120. Computing device 104 receives a user selection utilizing any network methodology as described herein. In an embodiment, computing device 104 may receive a user selection from a user input entered on graphical user interface 160 located on computing device 104. Computing device 104 logs a user entry wherein the user entry contains a user preference for a user selection. A user preference for a user selection may contain any review of a nourishment possibility 120 after a user consumed the nourishment possibility 120. A review may contain a description of how well a user liked or disliked a user selection, if the user tolerated the user selection, if the user experienced any side effects or symptoms after consuming the user selection, if the user would select the user selection again and the like. Computing device 104 logs a user entry such as by storing a user selection and/or a user preference for a user selection in memory located in computing device 104 and/or in a database. Computing device 104 incorporates a user selection and a user preference for a user selection in selector machine-learning process 152. Computing device 104 incorporates a user selection and/or a user preference for a user selection such as by including the user selection and/or the user preference for the user selection into a selector machine-learning model and/or as training data utilized to train subsequent selector machine-learning process 152. Computing device 104 receives an input containing a request for a group location. A group location includes any of the group locations as described above in more detail in reference to FIG. 1. For example, a group location may include the address and/or location of a party or an office location for example. Computing device 104 combines group nourishment possibility indexes 156 for a group location. Such information may be utilized by computing device 104 to coordinate ordering and/or delivery of nourishment possibilities to a group location.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
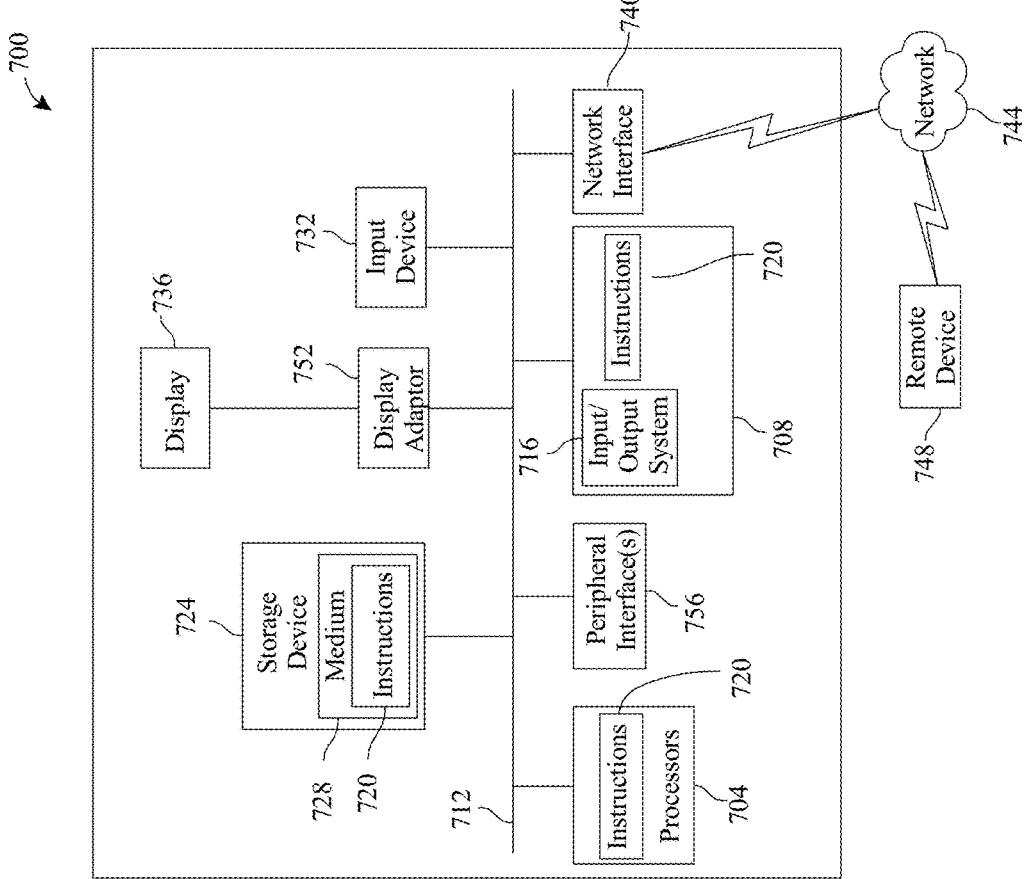
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Memory 708 may include various components (e.g., machine-readable media) including, but not limited to, a random access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for geographically tracking nourishment selection, the system comprising a computing device configured to:
   receive a location associated with a user's commute-from a user device;
   determine a plurality of nourishment possibilities within the location;
   locate a performance character associated with the user, wherein the performance character contains a nourishment score and at least a behavior relating to nourishment possibilities;
   generate a user profile wherein the user profile comprises the location, the plurality of nourishment possibilities, and the performance character;
   generate a first machine-learning process configured to utilize the user profile as an input, and output a plurality of corresponding nourishment possibility indexes, wherein generating the first machine-learning process comprises:
      providing a training set including a plurality of entries correlating user profile data to previous user selections of nourishment possibilities; and
      training the first machine-learning process as a function of the training data and a supervised machine-learning algorithm;
   generate, using the first machine-learning process, the plurality of nourishment possibility indexes as a function of the user profile and the first machine-learning process;
   grade, using a second machine-learning process, the plurality of nourishment possibilities using the plurality of corresponding nourishment possibility indexes and;
   wherein the system is implemented using a shared-nothing architecture which caches nourishment data to enable scalability of the system.

2. The system of claim 1, wherein the location further comprises a practiced route containing a frequency character.

3. The system of claim 1, wherein the location further comprises a multiple location route.

4. The system of claim 1, wherein the computing device is further configured to determine the plurality of nourishment possibilities using a nourishment preference.

5. The system of claim 1, wherein the computing device is further configured to calculate the nourishment score, wherein calculating the nourishment score further comprises:
   retrieving an element of data containing a logged nourishment entry; and
   generating a nourishment machine-learning process, wherein the nourishment machine-learning process utilizes the logged nourishment entry as an input, and outputs the nourishment score.

6. The system of claim 1, wherein the performance character further comprises a nourishment behavioral target.

7. The system of claim 1, wherein the computing device is further configured to:
   retrieve an element of user metric data; and
   generate the user profile utilizing the element of user metric data.

8. The system of claim 1, wherein the computing device is further configured to:
   display the plurality of graded nourishment possibilities on the computing device;
   receive a user selection selecting a first nourishment possibility;
   generate training data correlating previous user selections to nourishment possibilities;
   log a user entry wherein the user entry further comprises a user preference for the user selection; and
   incorporate the user selection and the user preference into the first machine-learning process.

9. The system of claim 1, wherein the computing device is further configured to:
   receive an input containing a request for a group location; and
   combine group nourishment possibility indexes for the group location.

10. A method of geographically tracking nourishment selection, the method comprising:
    receiving, by a computing device, a location associated with a user's commute from a user device;
    determining by the computing device, a plurality of nourishment possibilities within the location;
    locating by the computing device, a performance character associated with the user,
       wherein the performance character contains a nourishment score and at least a behavior relating to nourishment possibilities;

generating by the computing device, a user profile wherein the user profile comprises the location, the plurality of nourishment possibilities, and the performance character;

generating by the computing device, a first machine-learning process, wherein the first machine-learning process is configured to utilize the user profile as an input, and output a plurality of corresponding nourishment possibility indexes, wherein generating the first machine-learning process comprises:

providing a training set including a plurality of entries correlating user profile data to previous user selections of nourishment possibilities; and training the first machine-learning process as a function of the training data and a supervised machine-learning algorithm;

generating by the computing device and the first machine learning process, the plurality of corresponding nourishment possibility indexes as a function of the user profile and the first machine-learning process;

grading by the computing device and a second machine-learning process, the plurality of nourishment possibilities using the plurality of corresponding nourishment possibility indexes and;

wherein the system is implemented using a shared-nothing architecture which caches nourishment data to enable scalability of the system.

11. The method of claim 10, wherein the location further comprises a practiced route containing a frequency character.

12. The method of claim 10, wherein the location further comprises a multiple location route.

13. The method of claim 10, wherein determining the plurality of nourishment possibilities further comprises using a nourishment preference.

14. The method of claim 10, wherein determining the plurality of nourishment possibilities further comprises using a logged user performance metric.

15. The method of claim 10, wherein locating the performance character further comprises calculating the nourishment score, wherein calculating the nourishment score further comprises:

retrieving an element of data containing a logged nourishment entry; and generating a nourishment machine-learning process, wherein the nourishment machine-learning process utilizes the logged nourishment entry as an input, and outputs the nourishment score.

16. The method of claim 10, wherein the performance character further comprises a nourishment behavioral target.

17. The method of claim 10, wherein generating the user profile further comprises:

retrieving an element of user metric data; and generating the user profile utilizing the element of user metric data.

18. The method of claim 10 further comprising:

displaying the plurality of graded nourishment possibilities on the computing device;

receiving a user selection selecting a first nourishment possibility;

logging a user entry wherein the user entry further comprises a user preference for the user selection; and incorporating the user selection and the user preference into the-first machine-learning process.

19. The method of claim 10 further comprising:

receiving an input containing a request for a group location; and combining group nourishment possibility indexes for the group location.

20. The system of claim 1 further comprising, generating the training data from the previous user selection by associating each previous selection to a descriptor corresponding to a category of nourishment possibility and labeling the training data as a function of the associations.

* * * * *